(12) United States Patent
Doi et al.

(10) Patent No.: US 8,330,124 B2
(45) Date of Patent: Dec. 11, 2012

(54) FLUORESCENCE DETECTION DEVICE USING INTENSITY-MODULATED LASER LIGHT AND FLUORESCENCE DETECTION METHOD

(75) Inventors: Kyouji Doi, Tamano (JP); Shigeyuki Nakada, Tamano (JP); Hironori Hayashi, Tamano (JP); Kazuteru Hoshishima, Tamano (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 139 days.

(21) Appl. No.: 13/119,702

(22) PCT Filed: Sep. 16, 2009

(86) PCT No.: PCT/JP2009/004646
§ 371 (c)(1),
(2), (4) Date: Mar. 17, 2011

(87) PCT Pub. No.: WO2010/032452
PCT Pub. Date: Mar. 25, 2010

(65) Prior Publication Data
US 2011/0168917 A1    Jul. 14, 2011

(30) Foreign Application Priority Data

Sep. 19, 2008   (JP) .................................. 2008-240983

(51) Int. Cl.
*G01N 21/64* (2006.01)
*G01J 1/58* (2006.01)

(52) U.S. Cl. .................................. 250/461.1; 250/459.1
(58) Field of Classification Search ............... 250/459.1, 250/458.1, 214 R, 461.1
See application file for complete search history.

(56) References Cited

U.S. PATENT DOCUMENTS

| | | | |
|---|---|---|---|
| 5,270,548 A | 12/1993 | Steinkamp | |
| 5,317,162 A | 5/1994 | Pinsky et al. | |
| 5,504,337 A | 4/1996 | Lakowicz et al. | |
| 6,201,628 B1 | 3/2001 | Basiji et al. | |
| 7,541,598 B2 * | 6/2009 | Aasmul | ..................... 250/458.1 |
| 2008/0024779 A1 | 1/2008 | Aasmul | |

FOREIGN PATENT DOCUMENTS

| | | |
|---|---|---|
| JP | 2001-523830 A | 11/2001 |
| JP | 2007-240424 A | 9/2007 |
| JP | 2008-508506 A | 3/2008 |

* cited by examiner

*Primary Examiner* — David Porta
*Assistant Examiner* — Faye Boosalis
(74) *Attorney, Agent, or Firm* — Global IP Counselors, LLP

(57) ABSTRACT

A fluorescence detection device for a flow site meter emits laser light intensity-modulated in accordance with a modulation signal and acquires a fluorescent signal of fluorescence emitted from a measurement object that passes through a measurement point of the laser light. The fluorescence detection device generates, separately from the modulation signal, a reference signal having a frequency different from a frequency of the modulation signal and a phase in synchronization with a phase of the modulation signal. The fluorescence detection device determines a fluorescent relaxation time of the measurement object from the fluorescent signal by using the reference signal.

11 Claims, 5 Drawing Sheets

FLUORESCENCE DETECTION DEVICE USING INTENSITY-MODULATED LASER LIGHT AND FLUORESCENCE DETECTION METHOD

TECHNICAL FIELD

The present invention relates to a fluorescence detection device and a fluorescence detection method, in which a measurement object is irradiated with intensity-modulated laser light, fluorescence emitted from the measurement object by irradiation with the laser light is received to obtain a fluorescent signal, and the fluorescent signal is processed. More specifically, the present invention relates to a fluorescence detection device and a fluorescence detection method, which are applied to, for example, an analyzer, such as a flow cytometer for use in medical and biological fields, for analyzing measurement objects such as proteins, cells, DNA, or RNA in a short period of time by identifying each of the measurement objects with the use of fluorescence emitted from a fluorochrome.

BACKGROUND ART

A flow cytometer for use in medical and biological fields includes a fluorescence detection device that receives fluorescence emitted from a fluorochrome in a measurement object irradiated with laser light and identifies the type of measurement object. In the field of medicine, research on the interaction between proteins such as biological binding is being actively conducted. Particularly, research on the interaction between proteins using measurement of fluorescence resonance energy transfer (FRET) is being vigorously pursued. FRET is conventionally measured based on a change in fluorescence intensity, but in recent years, various flow cytometers that analyze measurement objects by utilizing difference in fluorescence relaxation time (fluorescence lifetime) have been proposed.

In a general flow cytometer, a flow is formed by allowing a suspension liquid containing measurement objects, such as biological substances (e.g., proteins, cells, DNA, RNA, or enzymes), labeled with fluorochromes (fluorescent reagents) to flow in a sheath liquid flowing under pressure through a tube at a flow rate of 10 m/sec or less. The flow cytometer receives fluorescence emitted from a fluorochrome attached to each of the measurement objects irradiated with laser light in the flow, and identifies the measurement object by identifying the fluorescence as a label.

Such a flow cytometer can measure, for example, the relative amount of a measurement object, such as DNA, RNA, an enzyme, or a protein, contained in an individual cell and analyze the property of the measurement object in a short period of time. Further, a cell sorter or the like is used to sort only identified cells or chromosomes in the living state in a short period of time after identifying a specific type of cell or chromosome based on fluorescence.

In this case, it is necessary to accurately identify a larger number of measurement objects in a short period of time based on the information of fluorescence.

Patent Document 1 discloses a device and method for identifying individual particles or cells labeled with different fluorochromes based on the lifetime (fluorescence relaxation time) of their fluorescence.

According to the Patent Document 1, laser light whose intensity has been modulated by a modulation signal from a modulator is emitted from a light source toward an irradiation port of a flow chamber to illuminate an individual particle or cell. Fluorescence emitted from an individual particle or cell is converted into a fluorescent signal by a photodetector and sent to two mixers.

On the other hand, the modulation signal from the modulator is sent to the two mixers via a variable phase shifter. At this time, the phase of the modulation signal to be supplied to one of the mixers is shifted by 90 degrees by a 90 degrees-phase shifter that shifts the phase of a signal by 90 degrees, and the phase of the modulation signal to be supplied to the other mixer is not shifted and therefore the modulation signal from the modulator is directly sent to the other mixer.

The fluorescent signal and the modulation signal sent to each of the mixers in such a manner as described above are mixed and passed through a low-pass filter to obtain a real part component and an imaginary part component which are information about the phase of the fluorescent signal. From the ratio between the real part component and the imaginary part component, fluorescence lifetime is calculated.

The Patent Document 1 describes that the flow cytometer can identify individual particles or cells based on the lifetime of their fluorescence.

In addition to the Patent Document 1, Patent Documents 2 and 3 also each disclose a flow cytometer that identifies individual particles or cells by determining the lifetime of their fluorescence from the phase delay of the fluorescence.

PRIOR ART DOCUMENTS

Patent Documents

Patent Document 1: U.S. Pat. No. 5,504,337
Patent Document 2: U.S. Pat. No. 5,270,548
Patent Document 3: U.S. Pat. No. 5,317,162

In the flow cytometers disclosed in the above-mentioned Patent Documents 1 to 3, a fluorescent signal and a modulation signal are mixed by a mixer to determine the phase of the fluorescent signal. The fluorescent signal used here is a signal of fluorescence emitted by irradiation with laser light whose intensity has been modulated by the modulation signal. Further, a mixer uses a signal split off from the modulation signal itself as a reference signal. Therefore, in a case where the modulation signal contains a noise component, a noise component synchronized with the fluorescent signal and the reference signal mixed by the mixer is superimposed, and thus a real part component and an imaginary part component, which are information about the phase delay of fluorescence, also contain a noise component as a signal. This leads to a problem in that the accuracy of calculation of fluorescence lifetime from the ratio between the real part component and the imaginary part component is reduced due to the influence of the noise component.

SUMMARY OF THE INVENTION

Problems to be Solved by the Invention

In order to solve the above problem, it is an object of the present invention to provide a device and method for detecting fluorescence by receiving fluorescence emitted from a measurement object irradiated with laser light whose intensity has been modulated at a predetermined frequency to obtain a fluorescent signal and processing the fluorescent signal, which are capable of calculating fluorescence relaxation time (fluorescence lifetime) with a higher degree of accuracy than ever before.

Means for Solving the Problems

An aspect of the present invention provides a fluorescence detection device using intensity-modulated laser light, which irradiates a measurement object with laser light, receives fluorescence emitted from the measurement object to obtain a fluorescent signal, and determines fluorescence relaxation time from the fluorescent signal. The device includes:

a laser light source unit emitting intensity-modulated laser light with which a measurement object is to be irradiated;

a light-receiving unit outputting a fluorescent signal of fluorescence emitted from the measurement object irradiated with the intensity-modulated laser light;

a signal generating unit generating a modulation signal having a predetermined frequency to modulate an intensity of laser light emitted from the laser light source unit and further generating, separately from the modulation signal, a reference signal having a frequency identical or almost identical with that of the modulation signal and synchronized with the modulation signal;

a signal processing unit performing first mixing processing to mix the reference signal and the fluorescent signal outputted by the light-receiving unit by irradiating the measurement object with the laser light whose intensity has been modulated using the modulation signal, and further performing, on a mixed signal resulted from the first mixing processing, first low-pass filtering to remove a signal component having a sum frequency of a frequency of the modulation signal and a frequency of the reference signal to output a fluorescent signal-based low-frequency signal; and a fluorescence detection unit calculating a phase of the fluorescent signal relative to the modulation signal using the fluorescent signal-based low-frequency signal to determine, from the calculated phase, a fluorescence relaxation time of the fluorescence emitted from the measurement object.

In the device, the signal generating unit can include a first oscillator generating a clock signal, a second oscillator generating the modulation signal in synchronization with the clock signal generated by the first oscillator, and a third oscillator generating the reference signal in synchronization with the clock signal.

The light-receiving unit includes, in addition to a light-receiving element receiving the fluorescence, a light-receiving element receiving side-scattered light obtained by irradiating the measurement object with the laser light to output a light-receiving signal obtained by receiving the side-scattered light. The signal processing unit performs, in addition to the first mixing processing and the first low-pass filtering performed on the fluorescent signal, second mixing processing to mix the light-receiving signal and the reference signal and second low-pass filtering on a mixed signal resulted from the second mixing processing to remove a signal component having the sum frequency to output a light-receiving signal-based low-frequency signal. The fluorescence detection unit can determine a phase of the light-receiving signal relative to the modulation signal using the light-receiving signal-based low-frequency signal, correct the phase of the fluorescent signal by subtracting the phase of the light-receiving signal from the phase of the fluorescent signal, and determine the fluorescence relaxation time of fluorescence emitted from the measurement object using the corrected phase.

Alternatively, the light-receiving unit includes, in addition to a light-receiving element receiving the fluorescence, a light-receiving element receiving side-scattered light obtained by irradiating the measurement object with the laser light to output a light-receiving signal obtained by receiving the side-scattered light. The signal processing unit performs, in addition to the first mixing processing and the first low-pass filtering performed on the fluorescent signal, second mixing processing to mix the light-receiving signal and the reference signal and second low-pass filtering on a mixed signal resulted from the second mixing processing to remove a signal component having the sum frequency to output a light-receiving signal-based low-frequency signal. When the modulation signal and the reference signal are different from each other in a frequency, the fluorescence detection unit can perform third mixing processing to mix the fluorescent signal-based low-frequency signal and the light-receiving signal-based low-frequency signal, calculate a corrected phase of the fluorescent signal based on a mixed signal resulted from the third mixing processing, and determine a fluorescence relaxation time of fluorescence emitted from the measurement object using the corrected phase.

The light-receiving unit preferably includes a neutral density filter or an opening plate for adjusting an intensity of light which is provided in front of a light-receiving surface of the light-receiving unit receiving the side-scattered light.

Another aspect of the invention provides a fluorescence detection method using intensity-modulated laser light, by receiving fluorescence emitted from a measurement object irradiated with laser light and determining fluorescence relaxation time from a fluorescent signal obtained from the received fluorescence. The method includes the steps of:

irradiating a measurement object with laser light whose intensity has been modulated by a modulation signal having a predetermined frequency;

receiving fluorescence emitted from the measurement object irradiated with the laser light by a detection means to acquire a fluorescent signal obtained by receiving the fluorescence;

generating, separately from the modulation signal, a reference signal having a frequency identical or almost identical with that of the modulation signal and a phase synchronized with a phase of the modulation signal;

performing, on a fluorescent signal obtained by the detection means by irradiating the measurement object with intensity-modulated laser light, first mixing processing using the reference signal and further performing first low-pass filtering to remove, from a mixed signal resulted from the first mixing processing, a signal component having a sum frequency of a frequency of the modulation signal and a frequency of the reference signal to generate a fluorescent signal-based low-frequency signal whose frequency is lower than that of the modulation signal; and calculating a phase of the fluorescent signal relative to the modulation signal using the fluorescent signal-based low-frequency signal to determine, from the calculated phase, a fluorescence relaxation time of fluorescence emitted from the measurement object.

When the fluorescence is received, side-scattered light obtained by irradiating the measurement object with the laser light is received in addition to the fluorescence and a light-receiving signal obtained by receiving the side-scattered light is outputted. The light-receiving signal is subjected to second mixing processing using the reference signal and second low-pass filtering is performed on a mixed signal resulted from the second mixing processing to remove a signal component having the sum frequency to output a light-receiving signal-based low-frequency signal. A phase of the light-receiving signal relative to the modulation signal is determined using the light-receiving signal-based low-frequency signal, the phase of the fluorescent signal is corrected by subtracting the phase of the light-receiving signal from a phase of the fluorescent signal-based low-frequency signal, and a fluorescence relaxation time of fluorescence emitted from the measurement object can be determined using the corrected phase.

When the fluorescence is received, side-scattered light obtained by irradiating the measurement object with the laser light is received in addition to the fluorescence and a light-receiving signal obtained by receiving the side-scattered light is outputted. The light-receiving signal is subjected to second mixing processing using the reference signal and second low-pass filtering is performed on a mixed signal resulted from the second mixing processing to remove a signal component having the sum frequency to output a light-receiving signal-based low-frequency signal. The third mixing processing is performed to mix the fluorescent signal-based low-frequency signal and the light-receiving signal-based low-frequency signal, a phase of the fluorescent signal is calculated based on a mixed signal resulted from the third mixing processing, and a fluorescence relaxation time of fluorescence emitted from the measurement object can be determined using the calculated phase.

Effect of the Invention

In an embodiment of the fluorescence detection device and the method according to the present invention, the modulation signal used for intensity modulation of the laser light with which the measurement object is to be irradiated and the reference signal used for the mixing processing are separately generated. Therefore, the fluorescent signal and the reference signal used for the mixing processing have few noise components synchronized with each other. Accordingly, the fluorescence relaxation time is determined from the signal resulted from the mixing processing with a higher degree of accuracy than ever before.

In an embodiment of the fluorescence detection device and the method, the phase of the fluorescent signal is corrected using the phase of light-receiving signal obtained by receiving the side-scattered light. Accordingly, a phase delay due to transmission time of the fluorescence signal and the light-receiving signal is removed from the corrected phase of the fluorescent signal, thereby making the fluorescence relaxation time more accurate.

In the fluorescence detection device, even if the frequency of the modulation signal and the frequency of the reference signal are set to be identical with each other, the set frequencies may not completely be identical. In this case, the fluorescent signal-based low-frequency signal may include AC component having information of a phase delay of the fluorescence instead of DC component, the AC component having, as a dominant frequency, a difference frequency between the frequency of the modulation signal and the frequency of the reference signal. To cope with the case, in an embodiment of the fluorescence detection device and the method, the phase of the fluorescent signal can be calculated by mixing the fluorescent signal-based low-frequency signal and the light-receiving signal-based low-frequency signal (the mixing processing performed on a hardware device or performed on software). Then, in the mixing processing a phase of the fluorescent signal-based low-frequency signal relative to the light-receiving signal-based low-frequency signal is calculated. Accordingly, a phase delay due to a difference between a transmission time of the reference signal and a transmission time of the fluorescent signal is not included in the calculated phase of the fluorescent signal.

BEST MODE FOR CARRYING OUT THE INVENTION

Hereinbelow, the present invention will be described in detail based on a flow cytometer suitably employing a fluorescence detection device according to the present invention using intensity-modulated laser light.

In the following description, a signal obtained by receiving fluorescence is referred to as a fluorescent signal and a signal obtained by receiving side-scattered light of laser light is referred to as a light-receiving signal.

Figure 1:
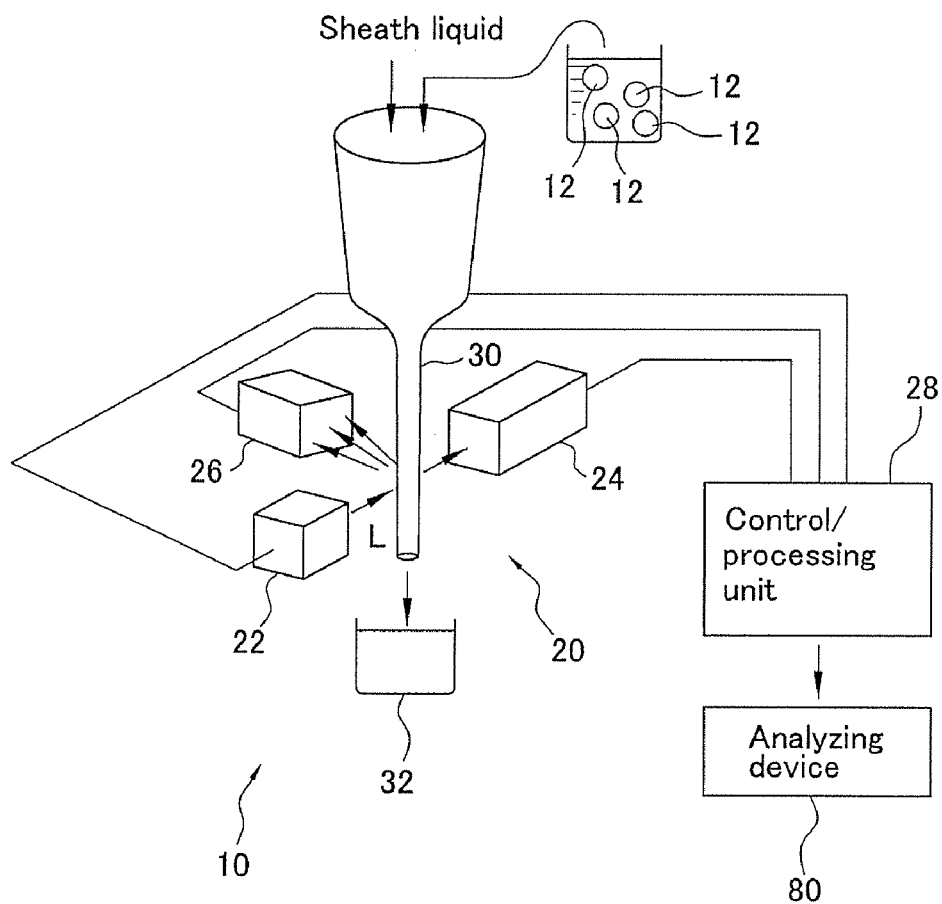
FIG. 1 is a schematic diagram illustrating the structure of a flow cytometer using a fluorescence detection unit according to the present invention using intensity-modulated laser light.
Figure 2:
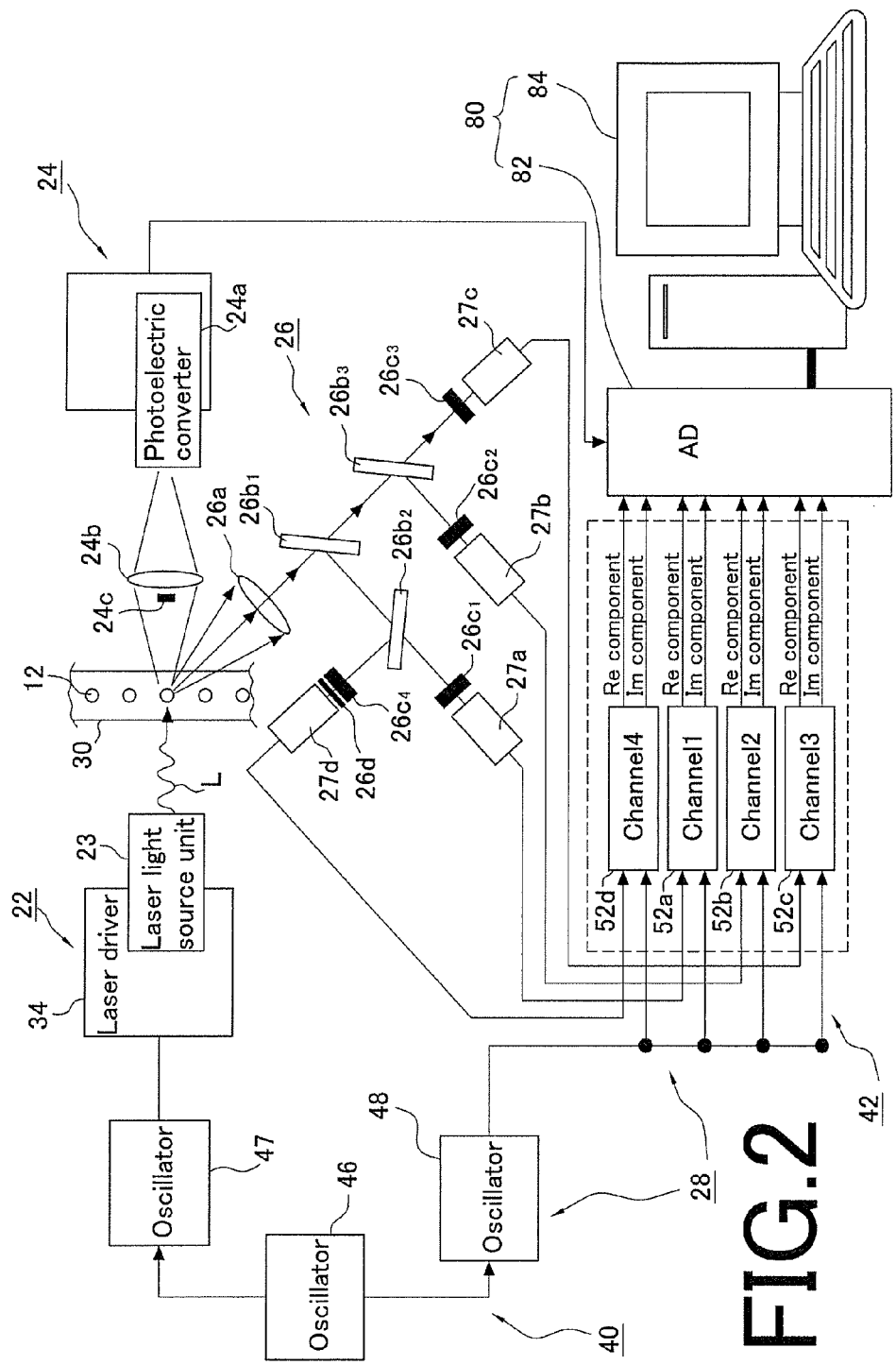
FIG. 2 is a diagram illustrating the structure of the flow cytometer illustrated in FIG. 1 in more detail.

FIG. 1 is a schematic diagram illustrating the structure of a flow cytometer 10 employing a fluorescence detection device using intensity-modulated laser light L. FIG. 2 is a diagram illustrating the structure of the flow cytometer 10 in more detail. The structure of the flow cytometer 10 will be described below.

The flow cytometer 10 includes a signal processing device 20 and an analyzing device 80. The function of each of the signal processing device 20 and the analyzing device 80 is summarized as follows. The signal processing device 20 irradiates, with laser light, samples 12, such as proteins to be measured, as measurement objects flowing in line through a flow cell. At this time, the flow cytometer 10 detects, as a fluorescent signal, fluorescence emitted from a fluorochrome labeling the sample 12 and processes the fluorescent signal. The analyzing device 80 analyzes a measurement object in the sample 12 using processing results obtained by the signal processing device 20.

The signal processing device 20 includes a laser emitting unit 22, light-receiving units 24 and 26, a control/processing unit 28, and a tube 30. The control/processing unit 28 includes a control unit that modulates the intensity of laser light emitted from the laser emitting unit 22 at a predetermined frequency and a signal processing unit that identifies a fluorescent signal from the sample 12. The tube 30 allows the samples 12 to flow in line in a sheath liquid forming a high-speed flow so as to form a flow cell.

As illustrated in FIG. 1, a collection vessel 32 is provided at the outlet of the tube 30. The flow cytometer 10 may be configured to have a cell sorter for separating a biological substance, such as a specific cell, in the sample 12 in a short period of time after irradiation with laser light L to sort the samples 12 into different collection vessels.

Each of the samples 12 is a measurement object such as a biological substance (e.g., a protein, a cell, DNA, RNA, or an enzyme) and is previously labeled with a fluorescent reagent (fluorochrome), and as illustrated in FIG. 1, a suspension liquid containing the samples 12 is prepared. The samples 12 contain, for example, two or more different kinds of biological substances. In this case, the two or more different kinds of biological substances are labeled with different known pigments, which emit fluorescence of different known wavelengths, as fluorochromes. This makes it possible for the flow cytometer 10 to determine characteristics such as biological binding between the two or more kinds of biological substances.

The samples 12 are not limited to biological substances, and may be, for example, microbeads, each having an artificial structure capable of binding to a specific biological substance.

The laser emitting unit 22 includes a laser light source unit 23 and a laser driver 34.

The laser light source unit 23 is a unit that emits laser light L having a predetermined wavelength. The laser light L is focused on a predetermined position in the tube 30 by a lens system (not illustrated), and the focus position is defined as a measurement point where the sample 12 is measured. The beam diameter of the laser light L at the measurement point is several tens of micrometers. It is to be noted that the laser light source unit 23 emits laser light L having a single wavelength, but may be configured to emit a single beam of laser combined of two or more beams of laser. In this case, the laser light source unit 23 uses, for example, a half mirror to combine two or more beams of laser into a single beam.

The laser light source unit 23 modulates, at a predetermined frequency, the intensity of CW (continuous wave) laser light L of constant intensity and emits intensity-modulated laser light L.

As a light source that emits laser light L, for example, a semiconductor laser is employed. The laser light L has an output of, for example, about 5 to 100 mW. On the other hand, the frequency (modulating frequency) at which the intensity of laser light L is modulated is, for example, 10 to 50 MHz, whose corresponding time period in a cycle is slightly longer than fluorescence relaxation time.

The laser driver 34 is connected to the control/processing unit 28 and is configured to control the output intensity of laser light L. Here, as will be described later, the intensity of laser light L is modulated at a predetermined frequency in response to a modulation signal.

The laser light source unit 23 emits laser light in a predetermined wavelength band so that laser light L can excite a fluorochrome to allow the fluorochrome to emit fluorescence within a specific wavelength band. The fluorochrome excited by laser light L is attached to the sample 12 such as a biological substance, and therefore when passing through the tube 30 as a measurement object, the sample 12 emits fluorescence at a specific wavelength by irradiation with laser light L at the measurement point.

The light-receiving unit 24 is arranged so as to be opposed to the laser light source unit 23 with the tube 30 being provided therebetween. The light-receiving unit 24 includes a photoelectric converter 24a, a collecting lens 24b, and a blocking plate 24c. The photoelectric converter 24a detects forward-scattered laser light L caused by the sample 12 passing through the measurement point and outputs a detection signal indicating the passage of the sample 12 through the measurement point. The blocking plate 24c is used to block laser light L so that the photoelectric converter 24a can receive forward-scattered light without directly receiving the laser light L.

The signal outputted from the light-receiving unit 24 is used as a trigger signal that informs an AD conversion board 82 (which will be described later) included in the analyzing device 80 on the timing of start of AD conversion, and informs an analyzing device main body 84 (which will be described later) on the timing of start of analysis.

On the other hand, the light-receiving unit 26 is located on the line of intersection of two planes, one of the planes passing through the measurement point and perpendicular to a direction in which laser light emitted from the laser light source unit 23 travels, and the other plane passing through the measurement point and perpendicular to a direction in which the samples 12 move in the tube 30. The light-receiving unit 26 includes photoelectric converters that receive fluorescence emitted from the sample 12 irradiated with laser light at the measurement point and side-scattered light of the laser light.

FIG. 2 schematically illustrates the structure of an example of the light-receiving unit 26.

The light-receiving unit 26 includes a lens system 26a that focuses a fluorescent signal from the sample 12, dichroic mirrors $26b_1$, $26b_2$, and $26b_3$, band-pass filters $26c_1$, $26c_2$, $26c_3$, and $26c_4$, a light intensity adjusting filter 26d, and photoelectric converters 27a to 27d such as photomultipliers.

The lens system 26a is configured to focus fluorescence incident on the light-receiving unit 26 on the light-receiving surfaces of the photoelectric converters 27a to 27d.

Each of the dichroic mirrors $26b_1$, $26b_2$, and $26b_3$ is a mirror that reflects fluorescence within a predetermined wavelength band but transmits other fluorescence.

The reflection wavelength bands and transmission wavelength bands of the dichroic mirrors $26b_1$, $26b_2$, and $26b_3$ and the band-pass filters $26c_1$, $26c_2$, $26c_3$, and $26c_4$ are set based on the wavelengths of fluorescence emitted from the sample 12 so that fluorescence within predetermined wavelength bands can pass through the dichroic mirrors $26b_1$, $26b_2$, and $26b_3$ and the band-pass filters $26c_1$, $26c_2$, $26c_3$, and $26c_4$. The dichroic mirror $26b_2$ is a mirror that reflects light within the wavelength range of side-scattered light of laser light but transmits light within a wavelength range including the wavelength of fluorescence.

Each of the band-pass filters $26c_1$, $26c_2$, $26c_3$, and $26c_4$ is a filter that transmits only fluorescence within a predetermined wavelength band. The band-pass filters $26c_1$, $26c_2$, $26c_3$, and $26c_4$ are provided in front of the photoelectric converters 27a, 27b, 27c, and 27d, respectively. The dichroic mirror $26b_2$ is provided in front of the light-receiving surfaces of the photoelectric converters 27a and 27d, and the photoelectric converter 27a receives light that has passed through the dichroic mirror $26b_2$, and the photoelectric converter 27d receives light that has been reflected by the dichroic mirror $26b_2$.

The transmission wavelength bands of the band-pass filters $26c_1$, $26c_2$, and $26c_3$ are set so as to correspond to the wavelength bands of fluorescence emitted from fluorochromes, respectively.

The light intensity adjusting filter 26d is a neutral density filter for adjusting the intensity of side-scattered light. An opening plate may be used instead of the neutral density filter. The light intensity adjusting filter 26d makes the level of a light-receiving signal derived from side-scattered light almost the same as the level of a fluorescent signal, which allows the phase of the light-receiving signal derived from the side-scattered laser light L to be used as a substitute for a phase delay resulted from light propagation or signal transmission. The phase of a light-receiving signal derived from the laser light L refers to a phase delay of a light-receiving signal derived from laser light L relative to a modulation signal. The phase of a light-receiving signal derived from laser light L is a delay resulting from the propagation time of laser light L or the transmission time of the light-receiving signal, and the phase of a fluorescent signal relative to a modulation signal is the sum of transmission delay resulting from propagation time or transmission time and time that elapses before fluorescence is emitted. However, the phase of a light-receiving signal varies depending on the level of a light-receiving signal derived from the side-scattered light. Therefore, in order to make the phase of a light-receiving signal almost the same as the transmission delay of a fluorescent signal resulting from propagation time or transmission time, the level of the light-receiving signal is adjusted by the light intensity adjusting filter 26d so that the level of the side-scattered light received by the photoelectric converter 27d becomes almost the same as the level of a fluorescent signal.

Each of the photoelectric converters 27a to 27d including a sensor equipped with, for example, a photoelectric multiplier is a sensor that converts light received by its photoelectric surface as a light-receiving surface into an electric signal. Each of the photoelectric converters 27a to 27c receives fluorescence having a predetermined wavelength because the wavelength range of light to be received by each of the photoelectric converters 27a to 27c is limited by the dichroic mirror and the band-pass filter. The photoelectric converter 27d receives side-scattered light of laser light L because the wavelength range of light to be received by the photoelectric converter 27d is limited by the dichroic mirror 26b$_2$. In this way, the light-receiving unit 26 receives fluorescence of three different wavelengths and side-scattered light of laser light L.

Here, the fluorescence and the side-scattered light are received by the light-receiving unit 26 as optical signals having signal information that has been subjected to intensity modulation at a given frequency, and therefore signals having a frequency corresponding to the frequency of intensity-modulated laser light L are outputted from the photoelectric converters 27a to 27d as fluorescent signals and a light-receiving signal. These fluorescent signals and light-receiving signal are sent to the control/processing unit 28.

The control/processing unit 28 is configured to have a signal generating unit 40 and a signal processing unit 42.

The signal generating unit 40 is a unit that generates a modulation signal for modulating the intensity of laser light at a predetermined frequency (intensity modulation) and a reference signal.

More specifically, the signal generating unit 40 includes an oscillator (first oscillator) 46, an oscillator (second oscillator) 47, and an oscillator (third oscillator) 48. Each of these oscillators may be formed in a circuit.

The oscillator 46 is a clock generator that generates a clock signal having a predetermined frequency.

The oscillator 47 generates a modulation signal for modulating the intensity of laser light L. The modulation signal generated by the oscillator 47 is allowed to have a single frequency component by a filter (not illustrated), and is supplied to the laser driver 34 via an amplifier. In the laser driver 34, a separately-prepared direct current is superimposed on the modulation signal and supplied to the laser light source unit 23.

As will be described later, the oscillator 48 generates a reference signal for use in determining fluorescence relaxation time. The frequency of the reference signal generated by the oscillator 48 is the same or almost the same as the frequency of the modulation signal generated by the oscillator 47, and the reference signal and the modulation signal are in synchronization with each other. The "in synchronization with each other" means that signals having the same phase at the start point of signal generation are generated. Therefore, the phases of both the signals periodically become 0 at the same time. The oscillators 47 and 48 each generate a signal in synchronization with the clock signal generated by the oscillator 46. Thus, the modulation signal and the reference signal are generated in synchronization with each other.

Further, the phrase "the frequency of the reference signal generated by the oscillator 48 is almost the same as the frequency of the reference signal generated by the oscillator 47" means that the difference obtained by subtracting the frequency of the reference signal from the frequency of the modulation signal is within a predetermined allowable error range. Here, the phrase "within a predetermined allowable error range" means that, for example, a difference frequency $\Delta f$ that is a shift of frequency of the reference signal relative to the frequency of the modulation signal is within 1% of the frequency of the modulation signal.

Each of the oscillators 46, 47, and 48 is enclosed in a separate housing that blocks electromagnetic wave. That is, the oscillators 46, 47, and 48 are respectively provided in independent electromagnetic environments. By providing each of the oscillators 47 and 48 in an independent electromagnetic environment, it is possible for the flow cytometer 10 to reduce the possibility that both the signals generated by the oscillators 47 and 48 contain a noise component generated by electromagnetic wave at the same time. This, as will be described later, makes it possible to determine fluorescence relaxation time with a high degree of accuracy.

As described above, the frequency of the modulation signal and the frequency of the reference signal are set to be the same, but it is difficult to make them exactly the same because the oscillators has an individual difference from each other and the characteristics of the oscillators slightly change depending on use conditions such as temperature. Therefore, as will be described later, the analyzing device 84 is configured to be able to perform processing even when the frequency of the modulation signal and the frequency of the reference signal are not identical with each other.

The signal generating unit 40 may use, instead of each of the oscillators 47 and 48, a PLL (Phase Locked Loop) circuit equipped with a phase comparator, a loop filter, a voltage control oscillating circuit, and a frequency divider. In this case, the PLL circuits can also generate a modulation signal and a reference signal in synchronization with each other.

The reason why the modulation signal and the reference signal are generated separately from each other by different oscillators is that, as compared to a case where one oscillator generates a modulation signal and a reference signal, a mixed signal obtained by mixing the modulation signal and the reference signal by an RF mixer (which will be described later) is less likely to be affected by an oscillator-originated noise component. Since the modulation signal and the reference signal are generated by different oscillators, there is little chance that the modulation signal and the reference signal, which are to be mixed together, contain a synchronized noise component. In addition, since each of the oscillators 46, 47, and 48 is enclosed in an independent housing that blocks electromagnetic wave, there is little chance that signals generated by them contain a common noise component.

The signal processing unit 42 is a unit that extracts information about the phase of fluorescence emitted from the sample 12 by irradiation with laser light with the use of the fluorescent signals and the light-receiving signal derived from side-scattered light outputted from the photoelectric converters 27a to 27d. More specifically, the signal processing unit 42 includes signal processing channels 1, 2, and 3 that process the fluorescent signals outputted from the photoelectric converters 27a to 27c, respectively, and a signal processing channel 4 that processes the light-receiving signal outputted from the photoelectric converter 27d. The contents of signal processing are the same in all the signal processing channels 1 to 4.

It is to be noted that the above-mentioned information about phase delay includes, for example, a real part component (Re component) and an imaginary part component (Im component) as obtained when the phase of a sine-wave signal is represented by a complex number.

The signal processing channel 1 of the signal processing unit 42 includes a processing circuit 52a. The signal processing channels 2 to 4 include processing circuits 52b to 52d, respectively.

Figure 3:
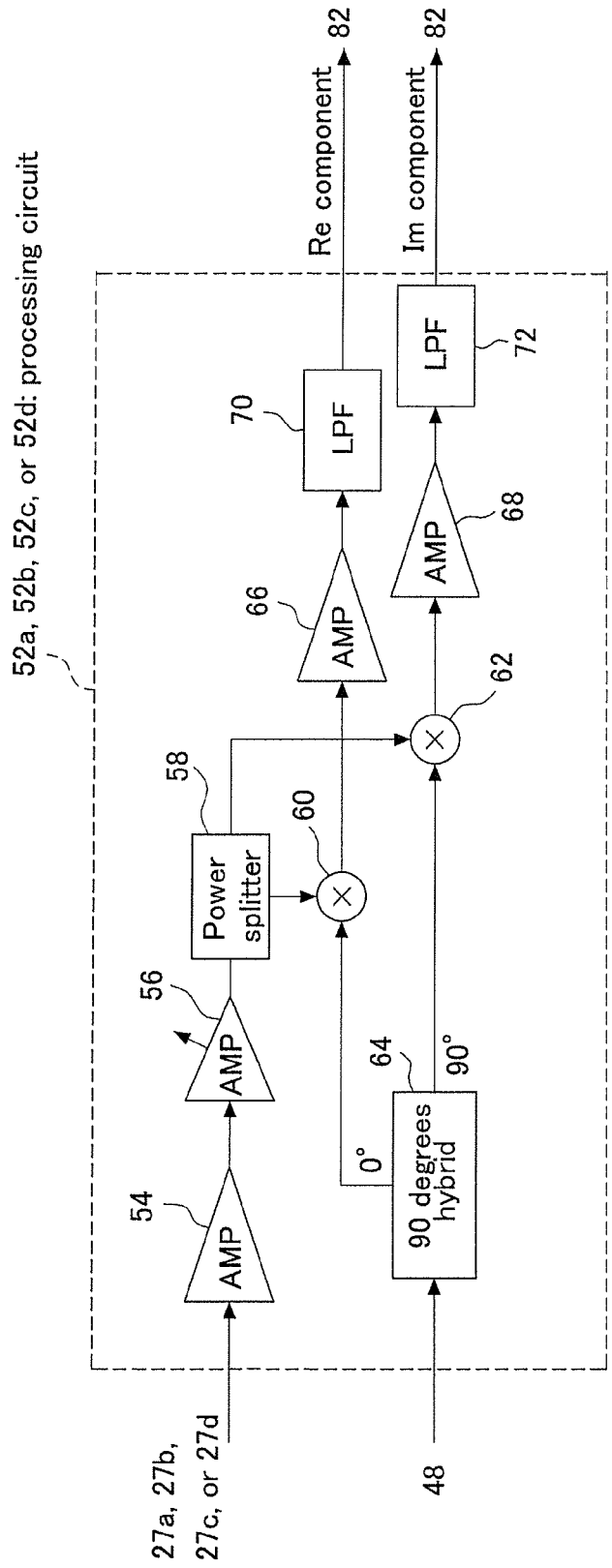
FIG. 3 is a diagram for explaining the structure of a signal processing unit of the flow cytometer illustrated in FIG. 1.

FIG. 3 is a diagram illustrating the structure of each of the processing circuits 52a, 52b, 52c, and 52d.

Each of the processing circuits 52a to 52d includes an amplifier 54 that amplifies a fluorescent signal (light-receiving signal), a variable amplifier 56, a power splitter 58 that splits an amplified fluorescent signal (light-receiving signal), RF mixers (first mixers) 60 and 62, a 90 degrees hybrid 64, amplifiers 66 and 68, and low-pass filters 70 and 72. It is to be noted that a variable attenuator may be used instead of the variable amplifier 56. A phase shifter may be used instead of the 90 degrees hybrid 64. When a phase shifter is used, a structure in which a signal is divided into two equal-phase signals to allow one of the signals to pass through the 90 degrees phase shifter or a structure using a switch for switching between a phase shift of 90 degrees and a phase shift of 0 degree is employed.

The fluorescent signal (light-receiving signal) sent from each of the photoelectric converters 27a to 27d is amplified by the amplifier 54, and is further amplified to a desired level by the variable amplifier 56 (in the case of using a variable attenuator, the amplified signal is attenuated). Further, the fluorescent signal (light-receiving signal) is split into two signals by the power splitter 58 and sent to the RF mixers 60 and 62.

On the other hand, the reference signal generated by the oscillator 48 is supplied to the 90 degrees hybrid 64 to generate a reference signal phase-shifted by 90 degrees and a reference signal not phase-shifted (with a phase shift of 0 degree). The reference signal phase-shifted by 90 degrees by the 90 degrees hybrid 64 is supplied to the RF mixer 62. On the other hand, the reference signal not phase-shifted is supplied to the RF mixer 60.

Each of the RF mixers 60 and 62 performs mixing processing to mix the supplied reference signal and the supplied fluorescent signal (light-receiving signal). As the RF mixers 60 and 62, active mixers or passive mixers such as double-balanced mixers are used.

In this embodiment, the reference signal is phase-shifted by 90 degrees and supplied to the RF mixer 62, but the fluorescent signal (light-receiving signal) may be phase-shifted by 90 degrees instead of the reference signal.

The amplifier 66 amplifies a mixed signal generated by the RF mixer 60 by mixing the reference signal and the fluorescent signal (light-receiving signal), and the amplifier 68 amplifies a mixed signal generated by the RF mixer 62 by mixing the reference signal and the fluorescent signal (light-receiving signal).

Each of the low-pass filters 70 and 72 has a cut-off frequency set to, for example, a value lower than the frequency of the modulation signal so as to remove, from the mixed signal resulted from the mixing processing, a high-frequency component including a sum frequency of the frequency of the reference signal and the frequency of the fluorescent signal (light-receiving signal) and transmit a low-frequency component. This makes it possible to allow the low-pass filter 70 to output a real part component (Re component) as information about the phase of the fluorescent signal (light-receiving signal) and to allow the low-pass filter 72 to output an imaginary part component (Im component) as information about the phase of the fluorescent signal (light-receiving signal). The signal of the Re component containing information about the phase of the fluorescent signal (light-receiving signal) and the signal of the Im component containing information about the phase of the fluorescent signal (light-receiving signal) are sent to the AD conversion board 82 of the analyzing device 80.

As described above, the frequency of the modulation signal and the frequency of the reference signal are the same or almost the same. Thus, the frequency of the fluorescent signal (light-receiving signal) and the frequency of the reference signal are the same or almost the same. Therefore, the signal of the real part component (Re component) outputted from the low-pass filter 70 and the signal of the imaginary part component (Im component) outputted from the low-pass filter 72 are signals having a constant value or an almost constant value. These signals contain information about the phase.

The real part component (Re component) outputted from the low-pass filter 70 and the imaginary part component (Im component) outputted from the low-pass filter 72 are sent to the analyzing device 80.

The analyzing device 80 includes the AD conversion board 82 (see FIG. 1) and the analyzing device main body (computer) 84. The AD conversion board 82 converts the real part component (Re component) and the imaginary part component (Im component) sent from each of the signal processing channels 1 to 4 into digital signals.

The AD conversion board 82 starts AD conversion of the real part component (Re component) and the imaginary part component (Im component) in response to the signal sent from the light-receiving unit 24 as a trigger signal. Then, the digitized real part component (Re component) and the digitized imaginary part component (Im component) are supplied to the analyzing device main body 84 and the analyzing device main body 84 starts analysis.

The analyzing device main body 84 determines the phase delay angle θ of fluorescence (phase angle of the fluorescent signal relative to the modulation signal) based on the real part component (Re component) and the imaginary part component (Im component) sent from the AD conversion board 82, and further determines fluorescence relaxation time from the phase delay angle θ. Based on the thus determined fluorescence relaxation time, the type of fluorochrome, from which the fluorescent signal outputted from the light-receiving unit 26 is derived, is identified.

The analyzing device main body 84 can determine the wavelength of fluorescence from which the fluorescence relaxation time is derived, by finding which signal processing channel outputting the real part component (Re component) and the imaginary part component (Im component) is associated with the determined fluorescence relaxation time. The fluorescence relaxation time of fluorescence emitted from a fluorochrome depends on the type of fluorochrome. Therefore, the analyzing device main body 84 can identify the type of fluorochrome, from which the fluorescence is derived, by determining the value of fluorescence relaxation time and finding which signal processing channel is associated with the determined fluorescence relaxation time. Further, information which type of fluorochrome is attached to the type of sample 12 can be recognized, so that the analyzing device main body 84 can identify the type of sample 12 that has passed through the measurement point by identifying the type of fluorescence. In a case where different two types of biological substances in the sample 12 are biologically bound, fluorescence emitted from a fluorochrome attached to one of the two types of biological substances and fluorescence emitted from another fluorochrome attached to the other biological substance are detected at almost the same time. In this case, the analyzing device main body 84 can identify the types of biological substances biologically bound to each other by identifying the types of fluorescence based on the values of fluorescence relaxation time. Such analysis is performed for each sample 12 passing through the measurement point, and therefore the analyzing device 80 can analyze the sample 12 comprehensively by statistically processing a plurality of obtained results.

The analyzing device main body 84 constitutes a fluorescence detection unit that calculates fluorescence relaxation time in the present invention, and is composed of a computer.

Figure 4:
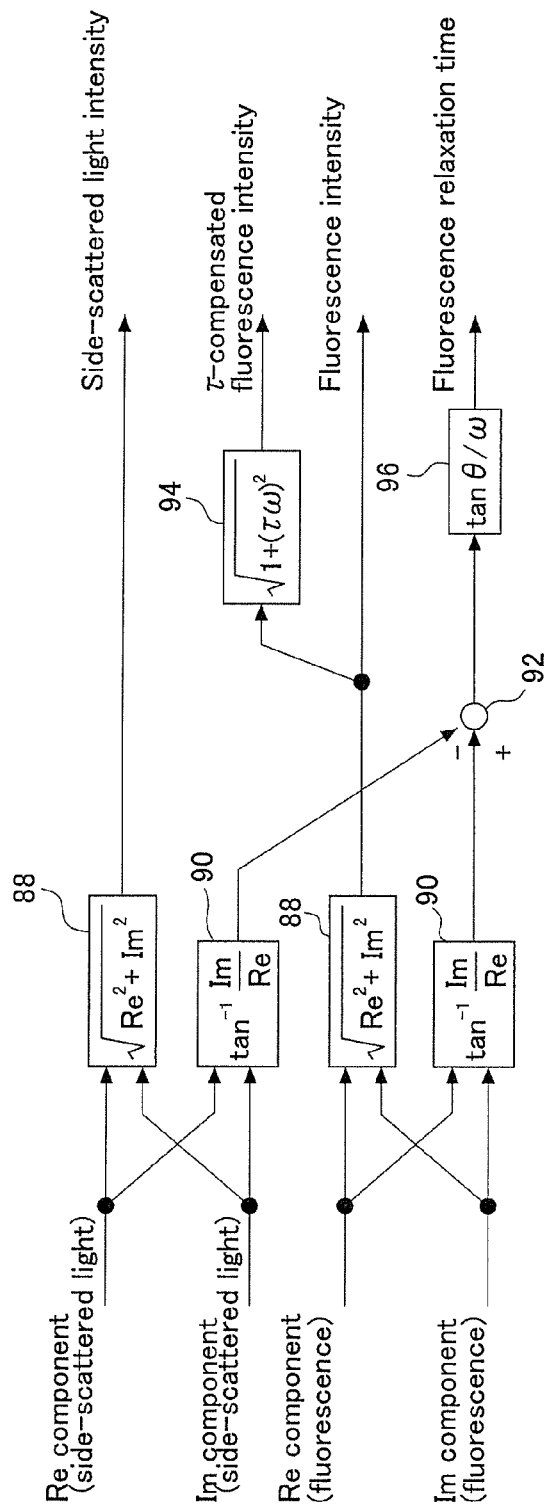
FIG. 4 is a diagram for explaining the contents of processing performed by an analyzing device of the flow cytometer illustrated in FIG. 1.

FIG. 4 is a diagram for explaining an example of contents of processing performed by the analyzing device main body 84.

The analyzing device main body 84 performs the processing illustrated in FIG. 4 after the real part component (Re component) and the imaginary part component (Im component) outputted from each of the signal processing channels are converted into digital data by the AD conversion board 82. The processing is performed by software.

Each of the contents of processing illustrated in FIG. 4 performed by software is modularized by a subprogram or subroutine. More specifically, the analyzing device main body 84 includes an amplitude calculation module 88, a phase calculation module 90, a phase delay calculation module 92, a compensated-fluorescence intensity calculation module 94, and a fluorescence relaxation time calculation module 96.

The example of contents of processing illustrated in FIG. 4 includes the contents of processing of the real part component (Re component) and imaginary part component (Im component) of fluorescence sent from the processing circuit 52a and the contents of processing of the real part component (Re component) and imaginary part component (Im component) of side-scattered light of laser light L sent from the processing circuit 52d, but does not include the contents of processing of the real part component (Re component) and the imaginary part component (Im component) sent from each of the processing circuits 52b and 52c. The contents of processing of the real part component (Re component) and the imaginary part component (Im component) sent from each of the processing circuits 52b and 52c are the same as the contents of processing of the real part component (Re component) and the imaginary part component (Im component) sent from the processing circuit 52a, and are therefore not illustrated in FIG. 4 and the description thereof will not be repeated here.

The real part component (Re component) and the imaginary part component (Im component) which relate to the phase of side-scattered light sent from the processing circuit 52d and the real part component (Re component) and imaginary part component (Im component) of fluorescence are all signals having a constant value or an almost constant value. These signals are sent to the amplitude calculation module 88 and the phase calculation module 90.

The amplitude calculation module 88 calculates the square-root of sum of squares of the signal of the real part component and the signal of the imaginary part component and outputs the calculated result as intensity. That is, the amplitude calculation module 88 outputs side-scattered light intensity and fluorescence intensity.

Further, the signal of the real part component and the signal of the imaginary part component are sent to the phase calculation module 90 to calculate $\tan^{-1}(Im/Re)$. This makes it possible to determine the phase of the light-receiving signal derived from side-scattered light and the phase of the fluorescent signal.

Further, the phase delay calculation module 92 determines the corrected phase of the fluorescent signal (phase delay of fluorescence) by subtracting the phase of the light-receiving signal determined by the phase calculation module 90 from the phase of the fluorescent signal determined by the phase calculation module 90. The reason why the phase of the fluorescent signal is corrected is to eliminate a phase delay, which is caused by the difference in transmission time from the transmission line of the fluorescent signal and by propagation time of laser light or fluorescence, using the phase of the light-receiving signal.

Then, the fluorescence relaxation time calculation module 96 calculates $\tan\theta/\omega$ using the corrected phase delay angle $\theta$, and outputs the calculated result as fluorescence relaxation time $\tau$. Here, $\omega$ is $2\pi f$ and f represents the frequency of the modulation signal.

The reason why the value of $\tan\theta/\omega$ can be regarded as fluorescence relaxation time $\tau$ is that fluorescence is emitted according to a first order lag response during a fluorescence relaxation process.

Further, the compensated-fluorescence intensity calculation module 94 calculates $(1+(\tau\omega)^2)^{(1/2)}$, and this calculated value is multiplied by the amplitude of fluorescence calculated by the amplitude calculation module 88 to determine $\tau$-compensated fluorescence intensity.

As described above, the analyzing device main body 84 calculates side-scattered light intensity, fluorescence intensity, fluorescence relaxation time $\tau$, and $\tau$-compensated fluorescence intensity, and performs statistical processing and analysis using the calculated results. As a matter of course, it is not always necessary for the analyzing device main body 84 to calculate all the side-scattered light intensity, fluorescence intensity, fluorescence relaxation time $\tau$, and $\tau$-compensated fluorescence intensity to perform statistical processing and analysis using all the calculated results. The analyzing device main body 84 preferably calculates at least fluorescence relaxation time $\tau$ to perform statistical processing and analysis using the fluorescence relaxation time $\tau$. It is to be noted that the side-scattered light intensity greatly varies depending on the structure of the sample 12, and therefore can be used as an indicator indicating the complexity of the structure of the sample 12.

The flow cytometer 10 is configured as above described.

In the flow cytometer 10, the oscillator 46 generates a clock signal, and the oscillator 47 generates a modulation signal in synchronization with the clock signal generated by the oscillator 46, and the oscillator 48 generates a reference signal in synchronization with the clock signal.

Therefore, a noise component contained in the modulation signal generated by the oscillator 47 and a noise component contained in the reference signal generated by the oscillator 48 are independent of each other, which makes it possible to, even when the fluorescent signal is mixed with the reference signal by each of the RF mixers 60 and 62, prevent a large noise component from being contained in the resulting mixed signal. This is because, unlike a conventional case, it is possible to prevent a large noise component from being contained in a mixed signal when a fluorescent signal containing a noise component is multiplied by a reference signal containing a noise component.

In the signal processing device 20 of such a flow cytometer 10, first, the oscillator 47 generates a modulation signal having a predetermined frequency in synchronization with the clock signal generated by the oscillator 46. Then, the modulation signal is subjected to predetermined processing by the laser driver 34, and is supplied to the laser light source unit 23. The laser light source unit 23 emits laser light L, whose intensity has been modulated at the frequency of the modulation signal, toward the measurement point. The laser light L is focused by a lens system (not illustrated) to be made a focused beam having a diameter of several tens of micrometers as measured at the measurement point.

In this state, the samples 12 are allowed to flow through the tube 30 so that a flow passing through the measurement point is formed. The flow has a diameter of, for example, 100 μm and a flow rate of, for example, 1 to 10 m/sec.

When laser light L is emitted toward the measurement point and the light-receiving unit 24 generates a detection signal indicating the passage of the sample 12 through the measurement point, this detection signal is sent to the analyzing device 80 as a trigger signal.

In response to the trigger signal, the oscillator 48 generates a reference signal in synchronization with the clock signal generated by the oscillator 46. The frequency of the reference signal is identical or almost identical with the frequency of the modulation signal.

The signal processing unit 42 performs mixing processing and low-pass filtering according to the signal processing circuit illustrated in FIG. 3 using the fluorescent signals and the light-receiving signal obtained by and sent from the photoelectric converters 27a to 27d and the reference signal. In this way, the signal processing unit 42 generates a real part component (Re component) and an imaginary part component (Im component) which are information about the phase of each of the fluorescent signals and the light-receiving signal derived from side-scattered light.

Here, the frequency of the modulation signal for modulating laser light L is, for example, 10 to 50 MHz.

The calculated real part component (Re component) and imaginary part component (Im component) are sent to the analyzing device 80.

The analyzing device 80 performs AD conversion to digitize the signal of the real part component (Re component) and the signal of the imaginary part component (Im component) sent from the signal processing unit 42. Then, the analyzing device main body 84 performs the processing illustrated in FIG. 4 to calculate side-scattered light intensity, fluorescence intensity, fluorescence relaxation time τ, and τ-compensated fluorescence intensity. The calculated results are used for statistical processing and analysis of the sample 12. It is to be noted that the analyzing device main body 84 calculates fluorescence relaxation time τ using the formula tan θ/ω based on the phase delay angle θ of the fluorescent signal, the phase delay angle θ being corrected based on the phase of the light-receiving signal derived from the side-scattered light.

Modified Example

Figure 5:
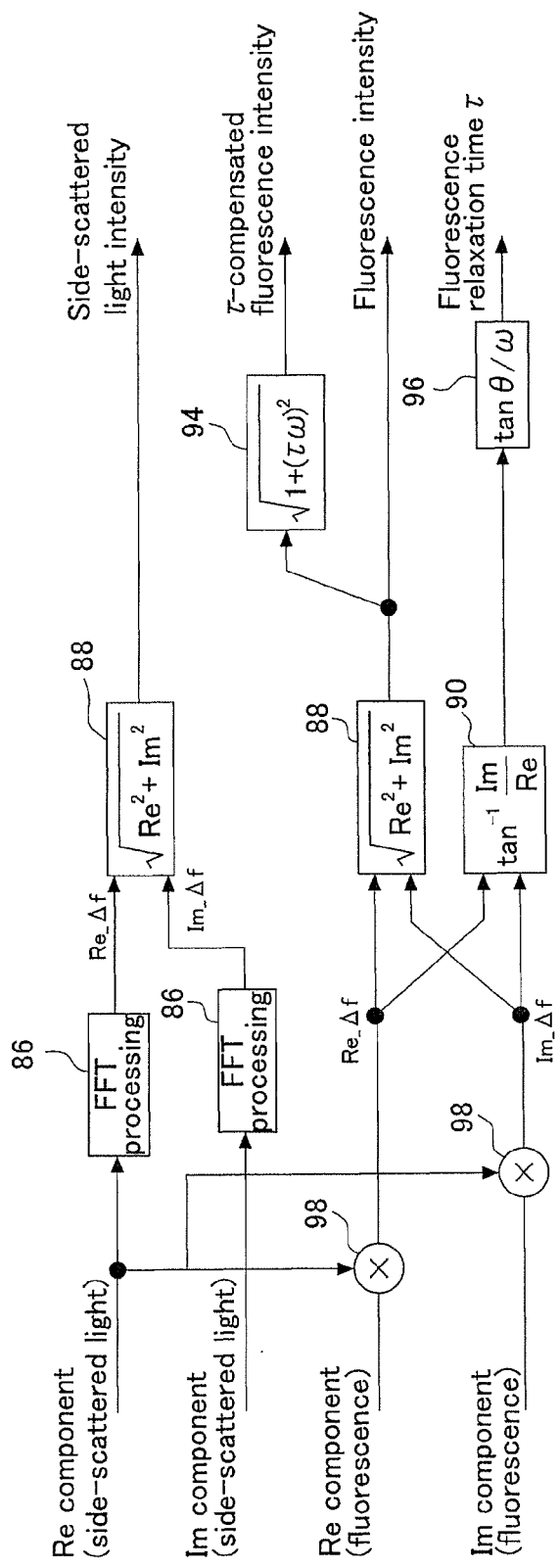
FIG. 5 is a diagram for explaining another example of contents of processing performed by the analyzing device, which are different from the contents of processing illustrated in FIG. 4.

FIG. 5 is a diagram for explaining an example of contents of processing performed by the analyzing device main body 84 which are different from the contents of processing illustrated in FIG. 4. The processing illustrated in FIG. 5 is performed using, in addition to the amplitude calculation module 88, the phase calculation module 90, the compensated-fluorescence intensity calculation module 94, and the fluorescence relaxation time calculation module 96 having their respective operations illustrated in FIG. 4, an FFT processing module 86 and a mixing processing module 98. In this modified example, the frequency of a signal generated by the oscillator 47 and the frequency of a signal generated by the oscillator 48 are almost identical, but there is a case where these frequencies vary depending on, for example, use conditions and are therefore not always exactly identical. That is, there is a case where a difference frequency Δf is generated. This modified example performs processing suitable for such a case.

This modified example can be configured to allow the analyzing device main body 84 to determine, when the frequency of the modulation signal and the frequency of the reference signal are almost identical on the order of megahertz but are not exactly identical and there is a difference between them, whether there is a nonnegligible difference frequency Δf to switch the processing illustrated in FIG. 4 to the processing illustrated in FIG. 5 based on a determination result. The nonnegligible difference frequency Δf refers to a difference frequency at the time when the value of the signal of the real part component (Re component) and the value of the signal of the imaginary part component (Im component) sent to the analyzing device 80 do not have almost constant values and vary within a measurement time during which the sample 12 passes through the measurement point. For example, the nonnegligible difference frequency Δf refers to 1/T or more as determined when the time that the sample 12 takes to pass through the measurement point is defined as T second.

In the case of the processing illustrated in FIG. 5, first, the FFT processing module 86 processes the real part component (Re component) and imaginary part component (Im component) of the light-receiving signal calculated by the signal-processing channel 4 to determine the value of the real part component at the difference frequency Δf (Re_Δf) and the value of the imaginary part component at the difference frequency Δf (Im_Δf). From these two values, the amplitude calculation module 88 calculates the amplitude of the light-receiving signal derived from side-scattered light and outputs the calculated amplitude as side-scattered light intensity.

On the other hand, the real part component (Re component) and imaginary part component (Im component) of the fluorescent signal obtained by the signal processing channel 1 are sent to the mixing processing module 98. Further, the real part component (Re component) of the side-scattered light is sent to the mixing processing module 98. The mixing processing module 98 mixes the real part component (Re component) and imaginary part component (Im component) of the fluorescent signal with the real part component (Re component) of the light-receiving signal derived from the side-scattered light. Then, a processing module (not illustrated) performs low-pass filtering using a cut-off frequency lower than a sum frequency of the frequency of the modulation signal and the frequency of the reference signal but higher than the difference frequency Δf to determine the value of the real part component at the difference frequency (Re_Δf) and the value of the imaginary part component at the difference frequency (Im_Δf).

For example, the real part component (Re component) of fluorescence sent to the mixing processing module 98 is defined as $\cos\{2\pi(f_1-f_2)\cdot t+2\pi f_1\cdot(\Delta t_1+\tau)\}$, where $f_1$ is the frequency of the modulation signal, $f_2$ is the frequency of the reference signal, $\Delta t_1$ is delay time of the fluorescent signal or light-receiving signal relative to the reference signal, and τ is fluorescence relaxation time.

At this time, the real part component (Re component) of side-scattered light is $\cos\{2\pi(f_1-f_2)\cdot t+2\pi f_1\cdot\Delta t_1\}$.

Therefore, when a mixed signal is generated from the Re component of the fluorescent signal by the mixing processing module 98 and is subjected to the above-mentioned low-pass filtering, a signal of $\cos\{2\pi\cdot f_1\cdot\tau\}$ is calculated as Re_Δf. Likewise, when a mixed signal is generated from the Im component of fluorescence by the mixing processing module 98 and is subjected to low-pass filtering, a signal of $\sin\{2\pi\cdot f_1\cdot\tau\}$ is calculated as Im_Δf.

Therefore, the values of these signals are sent to the amplitude calculation module 88 and the phase calculation module 90 to calculate fluorescence intensity and phase delay angle θ.

The fluorescence relaxation time calculation module 96 calculates tan θ/ω using the calculated phase delay angle θ, and the calculated result is regarded as fluorescence relaxation time τ. Here, ω is $2\pi f_1$. The reason why the value of tan θ/ω can be regarded as fluorescence relaxation time τ is that fluorescence is emitted according to a first order lag response during a fluorescence relaxation process.

Further, the compensated-fluorescence intensity calculation module 94 calculates $(1+(\tau\omega)^2)^{(1/2)}$, and the calculated value is multiplied by the amplitude of fluorescence calculated by the amplitude calculation module 88 to determine τ-compensated fluorescence intensity.

Further, the value of the real part component at the difference frequency Δf (Re_Δf) determined from the Re component of side-scattered light and the value of the imaginary part component at the difference frequency Δf (Im_Δf) determined from the Im component of side-scattered light are sent to the amplitude calculation module 88 to determine the amplitude and intensity of side-scattered light.

In this way, the analyzing device main body 84 calculates side-scattered light intensity, τ-compensated fluorescence intensity, fluorescence intensity, and fluorescence relaxation time τ, and performs statistical processing and analysis of the sample 12 using the calculated results.

Although the fluorescence detection device using intensity-modulated laser light and the fluorescence detection method according to the present invention have been described above in detail, the present invention is not limited to the embodiment described above. It should be understood that various changes and modifications may be made without departing from the scope of the present invention.

DESCRIPTION OF REFERENCE NUMERALS

10 flow cytometer
12 sample
20 signal processing device
22 laser emitting unit
23 laser light source unit
24, 26 light-receiving unit
24*b*, 26*a* lens system
26*b*$_1$, 26*b*$_2$, 26*b*$_3$ dichroic mirror
26*c*$_1$, 26*c*$_2$, 26*c*$_3$, 26*c*$_4$ band-pass filter
26*d* neutral density filter
27*a*, 27*b*, 27*c*, 27*d* photoelectric converter
28 control/processing unit
30 tube
32 collection vessel
34 laser driver
40 signal generating unit
42 signal processing unit
46, 47, 48 oscillator
52*a* to 52*d* processing circuit
54, 66, 68 amplifier
56 variable amplifier
58 power splitter
60, 62 RF mixer
64 90 degrees hybrid
70, 72 low-pass filter
80 analyzing device
82 AD conversion board
84 analyzing device main body
86 FFT processing module
88 amplitude calculation module
90 phase calculation module
92 phase delay calculation module
94 compensated-fluorescence intensity calculation module
96 fluorescence relaxation time calculation module
98 mixing processing module

The invention claimed is:

1. A fluorescence detection device using intensity-modulated laser light, which irradiates a measurement object with laser light, receives fluorescence emitted from the measurement object to obtain a fluorescent signal, and determines fluorescence relaxation time from the fluorescent signal, the device comprising:
    a laser light source unit emitting intensity-modulated laser light with which a measurement object is to be irradiated;
    a light-receiving unit outputting a fluorescent signal of fluorescence emitted from the measurement object irradiated with the intensity-modulated laser light;
    a signal generating unit generating a modulation signal having a predetermined frequency to modulate an intensity of laser light emitted from the laser light source unit and further generating, separately from the modulation signal, a reference signal having a frequency identical or almost identical with that of the modulation signal and synchronized with the modulation signal;
    a signal processing unit performing first mixing processing to mix the reference signal and the fluorescent signal outputted by the light-receiving unit by irradiating the measurement object with the laser light whose intensity has been modulated using the modulation signal, and further performing, on a mixed signal resulted from the first mixing processing, first low-pass filtering to remove a signal component having a sum frequency of a frequency of the modulation signal and a frequency of the reference signal to output a fluorescent signal-based low-frequency signal; and
    a fluorescence detection unit calculating a phase of the fluorescent signal relative to the modulation signal using the fluorescent signal-based low-frequency signal to determine, from the calculated phase, a fluorescence relaxation time of the fluorescence emitted from the measurement object.

2. The fluorescence detection device according to claim 1, wherein the signal generating unit comprises a first oscillator generating a clock signal, a second oscillator generating the modulation signal in synchronization with the clock signal generated by the first oscillator, and a third oscillator generating the reference signal in synchronization with the clock signal.

3. The fluorescence detection device according to claim 2, wherein the light-receiving unit comprises, in addition to a light-receiving element receiving the fluorescence, a light-receiving element receiving side-scattered light obtained by irradiating the measurement object with the laser light to output a light-receiving signal obtained by receiving the side-scattered light, and
    wherein the signal processing unit performs, in addition to the first mixing processing and the first low-pass filtering performed on the fluorescent signal, second mixing processing to mix the light-receiving signal and the reference signal and second low-pass filtering on a mixed signal resulted from the second mixing processing to remove a signal component having the sum frequency to output a light-receiving signal-based low-frequency signal, and
    wherein the fluorescence detection unit determines a phase of the light-receiving signal relative to the modulation signal using the light-receiving signal-based low-frequency signal, corrects the phase of the fluorescent signal by subtracting the phase of the light-receiving signal from the phase of the fluorescent signal, and determines the fluorescence relaxation time of fluorescence emitted from the measurement object using the corrected phase.

4. The fluorescence detection device according to claim 2, wherein the light-receiving unit comprises, in addition to a light-receiving element receiving the fluorescence, a light-receiving element receiving side-scattered light obtained by irradiating the measurement object with the laser light to output a light-receiving signal obtained by receiving the side-scattered light, and wherein the signal processing unit performs, in addition to the first mixing processing and the first low-pass filtering performed on the fluorescent signal, second mixing processing to mix the light-receiving signal and the reference signal and second low-pass filtering on a mixed signal resulted from the second mixing processing to remove a signal component having the sum frequency to output a light-receiving signal-based low-frequency signal, and wherein, when the modulation signal and the reference signal are different from each other in a frequency, the fluorescence detection unit performs third mixing processing to mix the fluorescent signal-based low-frequency signal and the light-receiving signal-based low-frequency signal, calculates a corrected phase of the fluorescent signal based on a mixed signal resulted from the third mixing processing, and determines a fluorescence relaxation time of fluorescence emitted from the measurement object using the corrected phase.

5. The fluorescence detection device according to claim 1, wherein the light-receiving unit comprises, in addition to a light-receiving element receiving the fluorescence, a light-receiving element receiving side-scattered light obtained by irradiating the measurement object with the laser light to output a light-receiving signal obtained by receiving the side-scattered light, and wherein the signal processing unit performs, in addition to the first mixing processing and the first low-pass filtering performed on the fluorescent signal, second mixing processing to mix the light-receiving signal and the reference signal and second low-pass filtering on a mixed signal resulted from the second mixing processing to remove a signal component having the sum frequency to output a light-receiving signal-based low-frequency signal, and wherein the fluorescence detection unit determines a phase of the light-receiving signal relative to the modulation signal using the light-receiving signal-based low-frequency signal, corrects the phase of the fluorescent signal by subtracting the phase of the light-receiving signal from the phase of the fluorescent signal, and determines the fluorescence relaxation time of fluorescence emitted from the measurement object using the corrected phase.

6. The fluorescence detection device according to claim 5, wherein the light-receiving unit includes a neutral density filter or an opening plate for adjusting an intensity of light which is provided in front of a light-receiving surface of the light-receiving unit receiving the side-scattered light.

7. The fluorescence detection device according to claim 1, wherein the light-receiving unit comprises, in addition to a light-receiving element receiving the fluorescence, a light-receiving element receiving side-scattered light obtained by irradiating the measurement object with the laser light to output a light-receiving signal obtained by receiving the side-scattered light, and wherein the signal processing unit performs, in addition to the first mixing processing and the first low-pass filtering performed on the fluorescent signal, second mixing processing to mix the light-receiving signal and the reference signal and second low-pass filtering on a mixed signal resulted from the second mixing processing to remove a signal component having the sum frequency to output a light-receiving signal-based low-frequency signal, and wherein, when the modulation signal and the reference signal are different from each other in a frequency, the fluorescence detection unit performs third mixing processing to mix the fluorescent signal-based low-frequency signal and the light-receiving signal-based low-frequency signal, calculates a corrected phase of the fluorescent signal based on a mixed signal resulted from the third mixing processing, and determines a fluorescence relaxation time of fluorescence emitted from the measurement object using the corrected phase.

8. The fluorescence detection device according to claim 7, wherein the light-receiving unit includes a neutral density filter or an opening plate for adjusting an intensity of light which is provided in front of a light-receiving surface of the light-receiving unit receiving the side-scattered light.

9. A fluorescence detection method using intensity-modulated laser light, by receiving fluorescence emitted from a measurement object irradiated with laser light and determining fluorescence relaxation time from a fluorescent signal obtained from the received fluorescence, the method comprising the steps of:

irradiating a measurement object with laser light whose intensity has been modulated by a modulation signal having a predetermined frequency;

receiving fluorescence emitted from the measurement object irradiated with the laser light by a detection means to acquire a fluorescent signal obtained by receiving the fluorescence;

generating, separately from the modulation signal, a reference signal having a frequency identical or almost identical with that of the modulation signal and a phase synchronized with a phase of the modulation signal;

performing, on a fluorescent signal obtained by the detection means by irradiating the measurement object with intensity-modulated laser light, first mixing processing using the reference signal and further performing first low-pass filtering to remove, from a mixed signal resulted from the first mixing processing, a signal component having a sum frequency of a frequency of the modulation signal and a frequency of the reference signal to generate a fluorescent signal-based low-frequency signal whose frequency is lower than that of the modulation signal; and calculating a phase of the fluorescent signal relative to the modulation signal using the fluorescent signal-based low-frequency signal to determine, from the calculated phase, a fluorescence relaxation time of fluorescence emitted from the measurement object.

10. The fluorescence detection method according to claim 9, wherein when the fluorescence is received, side-scattered light obtained by irradiating the measurement object with the laser light is received in addition to the fluorescence and a light-receiving signal obtained by receiving the side-scattered light is outputted, and wherein the light-receiving signal is subjected to second mixing processing using the reference signal and second low-pass filtering is performed on a mixed signal resulted from the second mixing processing to remove a signal component having the sum frequency to output a light-receiving signal-based low-frequency signal, and wherein a phase of the light-receiving signal relative to the modulation signal is determined using the light-receiving signal-based low-frequency signal, the phase of the fluorescent signal is corrected by subtracting the phase of the light-receiving signal from a phase of the fluorescent signal-based low-frequency signal, and a fluorescence relaxation time of fluorescence emitted from the measurement object is determined using the corrected phase.

11. The fluorescence detection method according to claim 9, wherein when the fluorescence is received, side-scattered light obtained by irradiating the measurement object with the laser light is received in addition to the fluorescence and a light-receiving signal obtained by receiving the side-scattered light is outputted, and wherein the light-receiving signal is subjected to second mixing processing using the reference signal and second low-pass filtering is performed on a mixed signal resulted from the second mixing processing to remove a signal component having the sum frequency to output a light-receiving signal-based low-frequency signal, and wherein third mixing processing is performed to mix the fluorescent signal-based low-frequency signal and the light-receiving signal-based low-frequency signal, a phase of the fluorescent signal is calculated based on a mixed signal resulted from the third mixing processing, and a fluorescence relaxation time of fluorescence emitted from the measurement object is determined using the calculated phase.

* * * * *